United States Patent
Dove

(10) Patent No.: US 9,351,487 B2
(45) Date of Patent: May 31, 2016

(54) POLYMERIC FILM FOR AGRICULTURAL PRODUCT STORAGE, CONTAINERS MADE THEREFROM AND RELATED METHODS OF AGRICULTURAL PRODUCT STORAGE

(71) Applicant: Rachel Dove, St. Marys, OH (US)

(72) Inventor: Rachel Dove, St. Marys, OH (US)

( * ) Notice: Subject to any disclaimer, the term of this patent is extended or adjusted under 35 U.S.C. 154(b) by 105 days.

(21) Appl. No.: 14/075,902

(22) Filed: Nov. 8, 2013

(65) Prior Publication Data

US 2014/0134223 A1 May 15, 2014

Related U.S. Application Data

(60) Provisional application No. 61/724,804, filed on Nov. 9, 2012.

(51) Int. Cl.
*A01N 63/00* (2006.01)
*A01N 25/00* (2006.01)
*A01N 25/34* (2006.01)
*A01N 27/00* (2006.01)
*A01N 53/00* (2006.01)

(52) U.S. Cl.
CPC ............... *A01N 25/34* (2013.01); *A01N 53/00* (2013.01); *A01N 63/00* (2013.01)

(58) Field of Classification Search
CPC ... A01N 65/00; A01N 2300/00; A01N 49/00; A01N 53/00; A01N 25/00; A01N 25/34
See application file for complete search history.

(56) References Cited

U.S. PATENT DOCUMENTS

| | | | |
|---|---|---|---|
| 2,952,874 A | 9/1960 | Doyle | |
| 3,009,200 A | 11/1961 | Voight | |
| 3,170,012 A | 2/1965 | Stinchcombe | |
| 3,300,555 A | 1/1967 | Bild | |
| 3,576,051 A | 4/1971 | Click et al. | |
| 3,778,387 A * | 12/1973 | Urbanie et al. | 502/401 |
| 3,813,279 A | 5/1974 | Varner | |
| 4,983,390 A * | 1/1991 | Levy | 424/404 |
| 5,795,644 A | 8/1998 | Delarosa | |
| 5,977,218 A * | 11/1999 | Bonora | 524/91 |
| 5,985,304 A | 11/1999 | Van Voris et al. | |
| 6,283,762 B1 | 9/2001 | Wiggins | |
| 6,316,520 B1 | 11/2001 | Hekal | |
| 6,322,873 B1 | 11/2001 | Orologio | |
| 6,547,468 B2 | 4/2003 | Gruenbacher et al. | |
| 6,607,739 B1 | 8/2003 | Wallo | |
| 8,372,418 B2 | 2/2013 | Dujardin et al. | |
| 2002/0095861 A1 | 7/2002 | Trussell | |
| 2004/0088904 A1* | 5/2004 | Laskey et al. | 43/124 |
| 2005/0089657 A1* | 4/2005 | Frandsen et al. | 428/35.7 |
| 2007/0157506 A1* | 7/2007 | Sadovski et al. | 43/114 |
| 2008/0312086 A1* | 12/2008 | Barazani | 504/347 |
| 2010/0192998 A1 | 8/2010 | Villers et al. | |
| 2011/0120005 A1* | 5/2011 | King et al. | 47/62 N |
| 2011/0152100 A1 | 6/2011 | Parrish et al. | |
| 2011/0240064 A1 | 10/2011 | Wales et al. | |

FOREIGN PATENT DOCUMENTS

| | | |
|---|---|---|
| GB | 2131740 A | 6/1984 |
| JP | H06-039972 A | 2/1994 |
| JP | 2010-285417 A | 12/2010 |
| WO | WO 9909824 A1 * | 3/1999 |
| WO | WO 1999/046175 A1 | 9/1999 |
| WO | WO 9944421 A1 | 9/1999 |
| WO | WO 2008122782 A1 * | 10/2008 |
| WO | WO 2009012887 | 1/2009 |
| WO | WO 2012007505 A2 * | 1/2012 |

OTHER PUBLICATIONS

Lord, Desiccant Dusts Synergize the Effect of Beauveria bassiana (Hyphomycetes: Moniliales) on Stored-Graiin Beetles, J. Econ. Entomol, 94(2): 367-372 (2001) abstract, p. 367, col. 1, para 1.

* cited by examiner

*Primary Examiner* — Frederick Krass
*Assistant Examiner* — Tracy Liu
(74) *Attorney, Agent, or Firm* — Roger A. Gilcrest

(57) ABSTRACT

The present invention includes polymeric laminate materials, containers made from same and methods for the storage of agricultural products and the like.

18 Claims, 7 Drawing Sheets

POLYMERIC FILM FOR AGRICULTURAL PRODUCT STORAGE, CONTAINERS MADE THEREFROM AND RELATED METHODS OF AGRICULTURAL PRODUCT STORAGE

RELATED APPLICATION DATA

This application claims the priority benefit of U.S. Provisional Application Ser. No. 61/724,804, filed Nov. 9, 2012, which is hereby incorporated in its entirety herein by reference.

FIELD OF THE INVENTION

The present invention relates to polymeric laminate materials, containers made from same and methods for the storage of agricultural products and the like. The present invention further relates to barrier films, in particular, barrier films exhibiting functional properties for the management of adverse conditions, pertaining particularly, but not limited to, food storage.

BACKGROUND OF THE INVENTION

Polymeric laminates may be used for the storage of agricultural products and the like, such as harvested grain, silage.

In agricultural production, it is beneficial to prevent post-harvest loss through the use of on-farm storage techniques and containers.

There are several concomitant problems attendant to on-farm storage of dry foodstuffs (e.g., grain and feedstock), such as the prevention of water ingress and the subsequent moisture accumulation in the surface layer of the grain adjacent the innermost layer of the container.

Free-standing storage containers for bagged agricultural commodities are prone to insect infestation and infestation development and growth of molds and resulting toxins. In addition, long term storage of dry foodstuffs typically is threatened by rodents and insects, as well as by bacteria fungus, such as aflatoxin. Accordingly, it is beneficial to provide on-farm storage containers that prevent or reduce the infestation and fungal growth. To reduce fungal growth, the containers should maintain some degree of oxygen permeability.

The container must also have sufficient strength and resiliency to withstand the forces associated with grain storage and transport.

In the preparation of polymeric materials of this type for these purposes, there has been a deficiency in the prior art in that, while the prevention of water ingress and associated moisture accumulation, as well as the use of rodent repellants, insecticides and fungicides are known, prior structural materials have not been able to achieve effective oxygen transmission (i.e., reduce oxygen flow toward the foodstuff and allow oxygen to flow away from the foodstuff), water vapor transmission and moisture management (i.e., water absorbancy) so as to be able to effectively reduce the risks associated with fungal growth, aflatoxin and mycotoxins; all while providing the other benefits of the active ingredients above.

Post-harvest losses due to poor handling, poor storage, insect infestations and mold or rot significantly hinder income generation for small-scale farmers. "In Tanzania, maize losses of up to 35% may occur due to *Prostephanus truncatus* (Larger Grain Borer) within 5 to 6 months if improperly stored (Mallya, 1992) and up to 60% losses may occur after 9 months of storage (Keil, 1988), a situation which may result in serious famine" according to the FAO's Paper on Insect Damage, Post Harvest Compendium. In Kenyan highlands, total losses due to pests in maize were estimated at 57% with insects being more important than disease (Grisley, 1997). In Zimbabwe, grain damage of 92% in stored maize was reported due to insect pests, treatment with malthion reduced damage by only 10% (Matrio, et al. 1992). Infestations of stored cowpeas can be as high as 90% in markets and in village stores (Alabeek, 1996). A wide variety of food stuffs are affected by insects, mold and fungi infestation is not limited to maize grains and pulses. Insect pests, in addition to fungal diseases, are responsible for 50% damage in cassava (Maninek, 1994). Losses of up to 70% in dried cassava roots after 4 months of storage were reportedly due to *P. truncatus*. (Hodges, et al., 1985).

Insect pests inflict their damage on stored products mainly by direct feeding. Some species feed on the endosperm, causing loss of weight and quality, while other species feed on the germ, resulting in poor seed germination and less viability (Malek & Parveen, 1989; Santus, et al. 1990). In addition to direct consumption of the product, insect pests contaminate their feeding media through excretion, molting, dead bodies and their own existence in the product which is not commercially desirable. Damage done by insect pests encourages infection with bacteria and fungal disease through transmission of their spores (Cravedi & Quaroni, 1982; E. Kundayo, 1988; Dunkel, 1980). The presence of insects also raises the stored product temperature, due to their feeding activity, resulting in hot spots (Appert, 1987; Mills, 1989). These "hot spots" can lead to condensation and excessive moisture, resulting in the growth of mold or fungi. Insects activity can have a profound effect on the spread of fungal diseases through transmitting the spores and increasing the surface area susceptible to fungal infection, which eventually increases production of mycotoxins (Dunkel, 1988).

Despite the physical damage of insect pests, infestations resulting from poor post-harvest storage can have economically devastating effects on farmers, communities, and the economies of several countries depending on exportation of maize, wheat and other food stuffs. For example, *P. truncatus* cost Tanzania roughly US $91 million annually in lost maize intended for consumption or export (Bionet International & Global Invasion Species Program). Farmers in sub-Sharan Africa are frequently forced to sell stored produce prematurely because of the deterioration due to insect damage that occurs if storage periods are extended (Global, et al. 1996, Brice et al. 1996, Marsland & Golob 1996, Donaldson, et al., 1996). Inability to store and protect post-harvest leads to significant income loss as farmers do not have the flexibility to wait for the higher price as the market fluctuates. The difficulties of on-farm food storage and the economic burden of post-harvest loss are devastating for farmers in developing countries, particularly due to the lack of available resources for building of storage units, the lack of information regarding insecticide/pesticide use, as well as lack of affordability.

On-farm storage difficulties and post-harvest losses occur mainly as a result of temperature, moisture, respiration of stored contents, infestation of insects, infestation of rodents and fumonisins, mycotxins and aflatoxins resulting from mold and fungi growth, due to lack of oxygen transmission and water vapor transmission of storage containers presently employed. Whether intended for human consumption, or used as animal food stock, stored product contamination poses serious health risks. Aflatoxin consumed by dairy cattle, though altered in their body, still remains toxic and shows up in the milk (Christensen & Meronuck, 1986, Gwinner, et al., 1996). *A. fumagatis* is report to result in high levels of abortion in cattle feeding on contaminated food; also infects human lungs (Darwish, et al., 1991; Pandey & Prasad 1993; Abud, et al., 1995).

The use of plastic sacks, bag storage, prefabricated iron halls and flexible plastic silos are increasingly gaining ground among farmers for short term storage (Peterson & Simila, 1990; Compton, et al., 1993; Bartali, 1994). However, none of the current storage mechanisms effectively manage the comprehensive set of factors including insect and pest repellency, barrier to oxygen, etc.

Accordingly, there remains a need for improved polymeric and woven laminates for dry on-farm storage of dry foodstuffs.

SUMMARY OF THE INVENTION

The present invention includes laminates and containers comprising same for the storage of agricultural products and the like, such as harvested grain and silage, as well as methods of storing grain for a period of time to permit on-farm storage and the subsequent economies of timely market approach. Films of the present invention may also find beneficial use in building applications, such as in grain storage facilities, such as in grain warehouse floor applications.

The laminates of the present invention may be produced using coextrusion, profile extrusion, thermoforming, film lamination, weaving, knitting and bonding machinery and processes, such as blow molding, film blowing and thermal point bonding and sheet bonding, stenter coating, known and used in the art.

Polymeric Laminate—Coextruded Version

In general terms, the invention includes a polymeric laminate comprising: (a) an outermost layer comprising a thermoplastic polymeric material containing at least one rodent repellent material, at least one pesticide and/or insecticide and an ultraviolet blocking material; (b) an innermost layer comprising a food grade polymer and an adhesive; and, interposed without respect to order between the outermost layer and innermost layers, the following layers: (c) an oxygen barrier intermediate layer comprising a thermoplastic polymeric material containing at least one additive that functions as a desiccant, a free radical scavenger or an oxygen barrier; and (d) a bio-composite absorbent/compatibilizer layer comprising a thermoplastic polymeric material containing at least one super-absorbent polymer and activated carbon, such as activated bamboo carbon charcoal or another antifungal additive (such as Triclosan). Examples are shown in FIGS. 1-1e.

It is preferred that the outermost layer comprises a first layer comprising a polyolefin, a rodent repellent and an ultraviolet blocking material; and a second layer comprising a thermoplastic polymeric material and at least one insecticide or pesticide material. It is further preferred that the bio-composite absorbent/compatibilizer layer comprises a first layer comprising at least one super-absorbent polymer; and a second layer comprising activated bamboo carbon.

The outermost layer may comprise a polyolefin selected from the group consisting of polypropylene, HDPE, LDPE, LLDPE, VLDPE and copolymers and homoploymers thereof.

The insecticide may be selected from the group consisting of synthetic pyrethroids, such as permethrin and deltamethrin and/or organophosphorous compounds, pirimiphos methyl, chlorpiriphos methyl, fenitrothion, malathion and/or composition or mixtures thereof and/or ethnobotanical mixtures, including without limitation neem plant or oil, sweet flag worm seed and peppers, geranium oil and menthol, and/or other plant-based materials.

In another related variation of the present invention, the polymeric laminate comprises: (a) an outermost layer comprising a polyolefin, a rodent repellent and an ultraviolet blocking material; (b) an innermost layer comprising a food grade polymer and an adhesive; and, interposed without respect to order between the outermost layer and innermost layers, the following layers: (c) an insecticide/pesticide intermediate layer comprising a thermoplastic polymeric material and either an insecticide or a pesticide material; (d) an oxygen barrier intermediate layer comprising ethylene vinyl alcohol and preferably EMMA with inorganic/organic additives; (e) a bio-composite absorbent layer comprising super-absorbent polymers; and (f) a bio-composite compatibilizer layer comprising activated bamboo carbon and a compatibilizer.

The compatibilizer(s) used in accordance with the present invention may include any compatibilizer effective to render the additive compatible with the surrounding polymer, such as those selected from the group consisting of chitin and citric acid.

In still another variant of the present invention, the invention includes a polymeric laminate comprising: (a) an outermost layer comprising a polyolefin, an insecticide/pesticide material, a cuticle desiccant and an ultraviolet blocking material; (b) an innermost layer comprising a food grade polymer and an adhesive; and, interposed without respect to order between the outermost layer and innermost layers, the following layers: (c) an rodent repellent intermediate layer comprising a thermoplastic polymeric material, a rodent repellent material and ethyl vinyl acetate; (d) an oxygen barrier intermediate layer comprising ethylene vinyl alcohol and/or EMMA and at least one inorganic/organic additives, (e) a bio-composite absorbent layer comprising at least one super-absorbent polymer(s); and (f) a bio-composite compatibilizer layer comprising activated bamboo carbon charcoal or another antifungal additive, and a compatibilizer.

Polymeric Laminate—Mesh Version

In still another variation of the present invention, the invention includes a polymeric laminate comprising, as shown for example in FIG. 2: (a) an outermost layer comprising a woven thermoplastic polymeric material containing at least one rodent repellent material and an ultraviolet blocking material, and a layer comprising at least one pesticide; (b) an innermost layer comprising a food grade polymer and an adhesive; and, interposed without respect to order between the outermost layer and innermost layers, the following layers: and (c) a bio-composite layer comprising a thermoplastic yarn mesh containing at least one super-absorbent polymer and activated carbon, such as an activated bamboo carbon charcoal or another antifungal additive.

It is preferred that the bio-composite layer be of an HDPE mesh containing at least one super-absorbent polymer, and a second layer comprising an HDPE mesh containing a bio-composite material and activated bamboo carbon.

Another variation of the present invention is a polymeric laminate comprising (a) an outermost layer comprising a thermoplastic polymeric material containing at least one rodent repellent material; (b) an innermost layer comprising a food grade polymer and an adhesive; and, interposed without respect to order between the outermost layer and innermost layers, the following layers: (c) a woven thermoplastic polymeric material; (d) a thermoplastic polymer layer containing at least one pesticide; (e) a bio-composite layer comprising a thermoplastic yarn mesh containing at least one super-absorbent polymer and activated carbon.

In one variation, the bio-composite layer comprises a thermoplastic mesh, such as HDPE or polypropylene mesh containing at least one super-absorbent polymer, and a second layer comprising an HDPE or polypropylene mesh containing a biocomposite material and activated bamboo carbon.

Still another variation of the invention is a polymeric laminate comprising (as exemplified in FIGS. 2b and 2c): (a) an outermost layer comprising a woven thermoplastic polymeric material containing at least one rodent repellent material and an ultraviolet blocking material, and a layer comprising at least one pesticide; (b) an innermost layer comprising a food grade polymer and an adhesive; and, interposed without respect to order between the outermost layer and innermost layers, the following layers: (c) a bio-composite layer comprising a thermoplastic yarn mesh containing at least one super-absorbent polymer and activated carbon such as activated bamboo carbon charcoal or another antifungal additive.

A further variation is a polymeric laminate comprising (see FIG. 3): (a) an outermost layer comprising a woven thermoplastic polymeric material containing at least one ultraviolet blocking material as well as, optionally, the rodent repellent and the at least one pesticide; (b) an innermost layer comprising a food grade polymer and an adhesive; and, interposed without respect to order between the outermost layer and innermost layers, the following layers: (c) a first bubble plastic thermoplastic polymeric material layer comprising bubbles containing at least one rodent repellent material; (d) a second bubble plastic thermoplastic polymeric material layer comprising bubbles containing at least one pesticide; (e) a non-woven or other equivalent layer, such as a filter membrane, that encapsulates cellulosic or other naturally absorbent materials and/or superabsorbent polymers, and (f) an optional bio-composite layer comprising a thermoplastic yarn mesh containing at least one super-absorbent polymer and activated carbon.

A variant of this embodiment additionally comprises a layer of a thermoplastic polymeric material containing calcium carbonate or equivalent material as a filler/blocking agent, and disposed between the second bubble plastic thermoplastic polymeric material layer and the a non-woven or other equivalent layer.

Preferably, the first bubble plastic layer comprises a polymer selected from the group consisting of LDPE, VLDPE, polypropylene or other suitable polymeric material, adhered to the outermost layer by an adhesive such as EVOH, and wherein second bubble plastic layer bubbles are provided with an insecticide in powder form, such as diatomaceous earth or other cuticle desiccant.

Yet another embodiment of the present invention includes a polymeric laminate comprising: (a) an outermost layer comprising a thermoplastic polymeric material containing at least one ultraviolet blocking material as well as, optionally, the rodent repellent and at least one pesticide; (b) an innermost layer comprising a food grade polymer and an adhesive; and, interposed without respect to order between the outermost layer and innermost layers, the following layers: (c) a first bubble plastic thermoplastic polymeric material layer comprising bubbles containing at least one rodent repellent material; (d) a second bubble plastic thermoplastic polymeric material layer comprising bubbles containing at least one pesticide; (e) a bio-composite absorbent layer comprising at least one super-absorbent polymer(s); and (f) a bio-composite compatibilizer layer comprising activated carbon such as bamboo carbon, and a compatibilizer.

With respect to all of the embodiments of the present invention, it will be recognized that the layered substrates, or mixtures thereof may include recycled material in place of or in addition to biobased material in an amount of up to 100% of the biobased material. As used herein, "recycled" materials encompass post-consumer recycled (PCR) materials, post-industrial recycled (PIR) materials, and a mixture thereof.

A Polymeric Storage Container for Harvested Agricultural Products

The present invention also includes a polymeric storage container for harvested agricultural products, the container comprising a polymeric laminate according to any of embodiments of the invention. These may be produced by any methods and through the use of machinery known and used in the art for creating polymeric bags and other containers made from or incorporating polymeric sheet or woven sheet material, into or supported by a framed structure.

System for Storage of Harvested Agricultural Products

A system for storage of harvested agricultural products, the system involving the use of such laminates or containers made therefrom and/or bags for on-farm storage at a farm.

Laminates of the present invention may be used in a system and method for free-standing hermetic storage of bulk, boxed or bagged commodities, such as that described for instance in U.S. Pat. No. 8,141,328, which is hereby incorporated herein by reference.

The present invention may also be considered an improvement upon the materials and methods described in Korean Patent Application No. KR10109267, which is hereby incorporated herein by reference.

The foregoing and other objects, features, and advantages of this invention will become more readily apparent from the following detailed description of a preferred embodiment which proceeds with reference to the accompanying drawings, wherein the preferred embodiment of the invention is shown and described, simply by way of illustration of the best mode contemplated of carrying out the invention.

As will be realized, the invention is capable of other and different embodiments, and its several details are capable of modifications in various obvious respects, all without departing from the invention. Accordingly, the drawings and description are to be regarded as illustrative in nature, and not as restrictive. It will also be appreciated that the detailed description represents the preferred embodiment of the invention, and that individual steps of the process of the invention may be practiced independently so as to achieve similar results; and likewise that variations of the described laminates and containers may be made by modifications in the design or manufacturing process to achieve similar results.

DETAILED DESCRIPTION OF THE PREFERRED EMBODIMENTS

In accordance with the foregoing summary, the following provides a detailed description of the preferred embodiment, which is presently considered to be the best mode thereof.

As used throughout this application, the term "polymer" refers to a material which is the product of a polymerization or copolymerization reaction of natural, synthetic or combined natural and synthetic monomers and/or co-monomers and is inclusive of homopolymers, copolymers, terpolymers, etc. In general, the layers of the multilayer film described in the present application may comprise a single polymer, a mixture of a single polymer and non-polymeric material, a combination of two or more polymers blended together, or a mixture of a blend of two or more polymers and non-polymeric material. It will be noted that many polymers may be synthesized by the mutual reaction of complementary monomers. It will also be noted that some polymers are obtained by the chemical modification of other polymers such that the structure of the macromolecules that constitute the resulting polymer may be thought of as having been formed by the homopolymerization of a hypothetical monomer.

As used throughout this application, the term "thermoplastic" refers to a polymer or polymer mixture that softens when exposed to heat and then returns to its original condition when cooled to room temperature. In general, thermoplastic materials may include natural or synthetic polymers.

Figure 1:
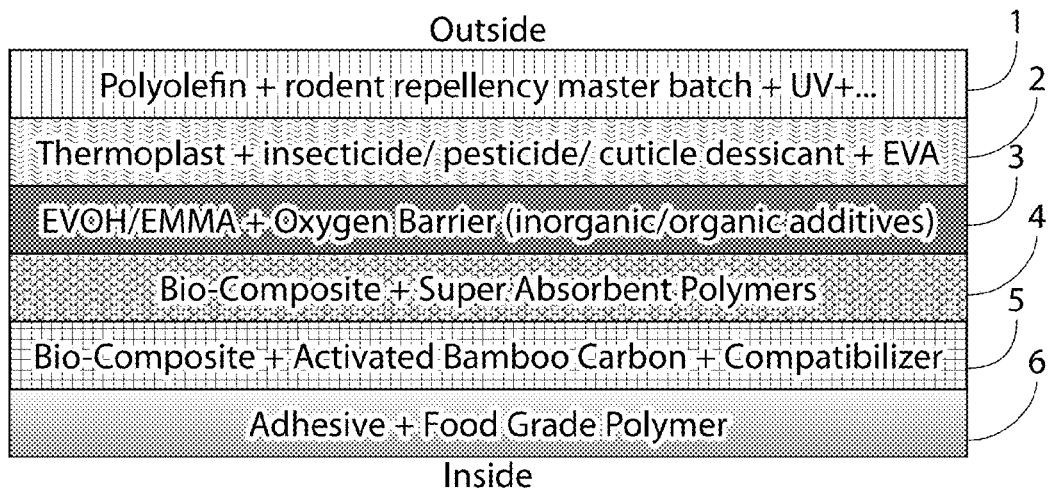
FIG. 1 is a schematic of a polymeric laminate in accordance with one embodiment of the present invention.

FIG. 1 is a schematic of a polymeric laminate in accordance with one embodiment of the present invention which may be produced by co-extrusion and film-blowing, such as by using centurion equipment commercially available from Kung Hsing of Taiwan. This may be made as a multi-layer coextrusion wherein the substrate is not limited to the number or order of the layers.

The typical thickness range of the laminates of the present invention made from coextrusion is from about 100 microns to 600 microns, although other thicknesses may be produced. The thicknesses of the individual layers may be determined to obtain overall laminate dimensions, but typically will be in the general range of 80 to 150 microns.

The outermost layer 1 may be produced of a thermoplastic material, such as a polyolefin selected from the group consisting of polypropylene, HDPE, LDPE, LLDPE, VLDPE and copolymers and homoploymers thereof. An example of the LLDPE is PLEXAR 800 commercially available from Lyondell Basel.

The rodent repellent(s) that may be used in accordance with the present invention may include without limitation any synthetic or natural rodent repellent miscible with the polyolefin and/or thermoplastic base layer, such as denatonium benzoate, denatonium benzoate, trinitrobenezene-aryl amine complexes, and tributyl tin chloride. Natural rodent repellents may include, without limitation, salicylic ester, menthol, corn mint oil, eucalyptus, camphor, terpene, peppermint oil, citronella oil, rosemary oil, clove oil, geranium oil, cayenne pepper, methyl nonyl ketone, or combinations thereof.

The ultraviolet blocking material(s) may be any material effectively miscible with the base polymer, and in an effective amount known in the art such as, for instance, from about 2% to about 5% percent by weight. An example of such a material is Optiblock 10 commercially available from Specialty Minerals, Inc.

The pesticide intermediate layer 2 may comprise a thermoplastic polymeric material or polyolefin, and at least one insecticide or pesticide material that may include any synthetic or natural insecticide or pesticide compatible with the polymeric material, provided in an effective amount to reduce or eliminate infestation. Examples include those selected from the group consisting of synthetic pyrethroids, such as permethrin. Most preferably, the insecticide is a combination of pirimiphos-methyl (sold commercially under the name Actellic Superdust), with permethrin at a concentration of 3% by weight and pirimiphos-methyl at 14% by weight, or other silicone dioxide plus synthetic pyrethroids or mixtures thereof.

The insecticide may also include a cuticle desiccant material, or materials that sterilize insects, inhibit their growth or retard their reproduction.

The thermoplastic polymeric material may be selected from among any material that may be amenable to co-extrusion while being able to contain the active ingredients at an effective level. Examples may include ethyl vinyl acetate or a thermoplastic polymer mixed with natural starches so as to form a biocomposite. An example of such a starch-blended polyester is Ecoflex from BASF.

The oxygen barrier intermediate layer 3 preferably may comprise any thermoplastic material, though it is preferred to use ethyl vinyl alcohol (EVOH), ethylene methyl acrylic copolymer (EMMA) or ethylene-methacrylic acid (EMAA) owing to their increased adhesion with the other layers. An example of such an EMMA material is PXL 164 commercially available from Lyondell Basel as PLEXAR. This layer includes at least one oxygen barrier material, such as inorganic or organic additives that function as desiccants, free radical scavengers or oxygen barriers, and provided in effective amount to penetrating from the outside layer. This amount will vary with the foodstuff volume to laminate surface area ratio of the specific application, but generally will be in the range of from about 2% to 75% by weight. Such inorganic additives may include iron, ascorbic acid, calcium hydroxide, activated carbon, sodium chloride, potassium chloride, magnesium oxide, titanium oxide, aluminum oxides, chromium oxide, calcium oxide, silica, bentonite, zeolites, montmorillonite, mullites, wollastonites and agalmatolite clay.

Organic additives may include such substances as are known in the field, such as compatibilizers metal alcoholates and alkoxysilanes. Typical content of these materials will be in the range of from about 3% to about 25% percent by weight, or otherwise, depending upon the nature of the material to be incorporated into the polymeric structural layer.

The bio-composite absorbent layer 4 comprises one or more super-absorbent polymers, such as sodium polyacrylates commercially available from Shanghai Dinghan Chemical Co., Shanghai, PRC, or from Teijin Limited of Taiwan, and provided in an effective amount to absorb water issuing from the dry foodstuff to be contained. This amount may be determined by reference to local climatic conditions and the amount of moisture to be generated through transpiration of the stored product, such as in the context of contained corn or maize.

The bio-composite absorbent layer 4 may preferably be provided with micro perforations of a valve type to manage oxygen transmission and moisture vapor transmission, in accordance with methods known in the art. Such valve perforations, when preferably placed at approximately a 45 degree angle to the laminate surface, are effective to allow water to migrate from this layer to reach the outside of the laminate, yet prohibitive of in-flow.

The bio-composite compatibilizer layer 5 comprises a thermoplastic polymer material as the base material, with addition of activated carbon, preferably activated bamboo carbon, and a compatibilizer, in an amount effective to such as chitin, citric acid, such as Ciroflex A4, commercially available from Vertellus. Typical content of these materials will be in the range of from about 1% to about 25% percent by weight.

Any of the foregoing layers 3, 4 or 5 may contain a blocking ingredient, such as calcium carbonate, silica or talc, that restrict the mobility of the pesticide or rodent repellent ingredient to prevent them reaching the contained dry foodstuff.

The innermost layer 6 comprises preferably a food grade polymer and an adhesive adapted to affix this layer to the immediately adjacent intermediate layer, such as layer 5. Examples of food grade polymers may include Sabic 6135 NE.

It will be understood that each of the individual layers shown and described may be combined and/or amalgamated along with the active ingredients contained within or affixed to each such layer so as to produce a functional laminate not inconsistent with the integration of the constituent layers and the function of the active ingredients. Examples of such variation are described herein.

Figure 1A:
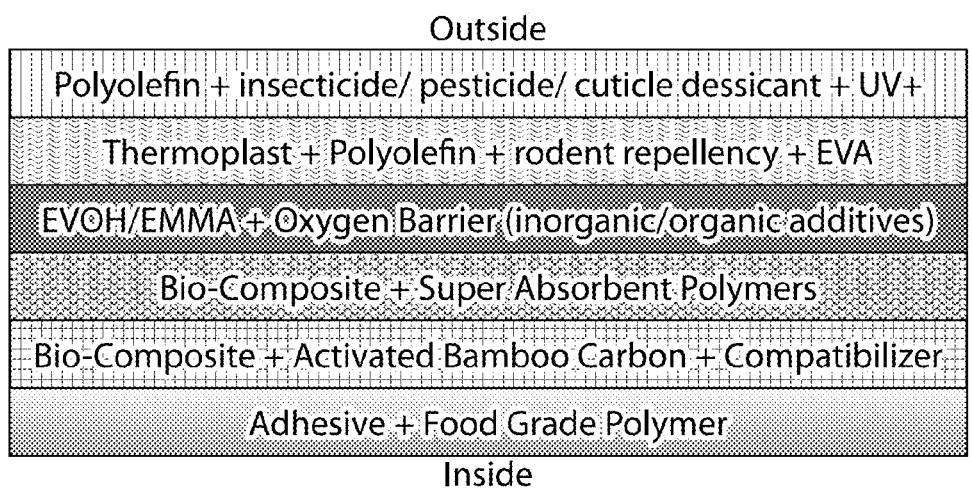
FIG. 1a is a schematic of a polymeric laminate in accordance with an alternative embodiment of the present invention.

FIG. 1a is a schematic of a polymeric laminate in accordance with an alternative embodiment of the present invention. This embodiment is similar to that of FIG. 1 except that the outermost layer contains the pesticide and the UV blocker ingredient, while the first intermediate layer contains the rodent repellency ingredient(s).

Figure 1B:
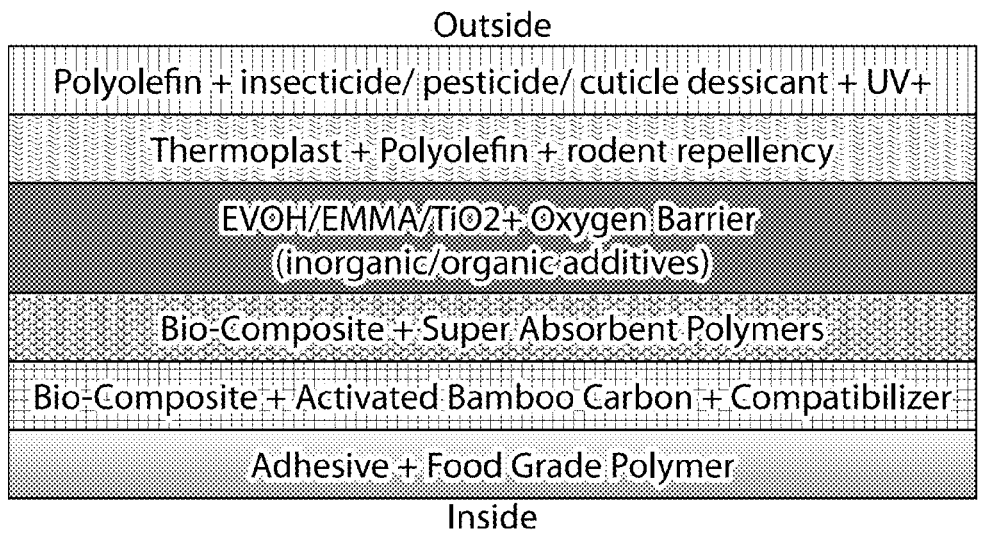
FIG. 1b is a schematic of a polymeric laminate in accordance with yet another alternative embodiment of the present invention.

FIG. 1b is a schematic of a polymeric laminate in accordance with yet another alternative embodiment of the present invention. This embodiment is similar to that of FIG. 1 except that layers 1 and 2 have been effectively combined by being coextruded as a single layer.

Figure 1C:
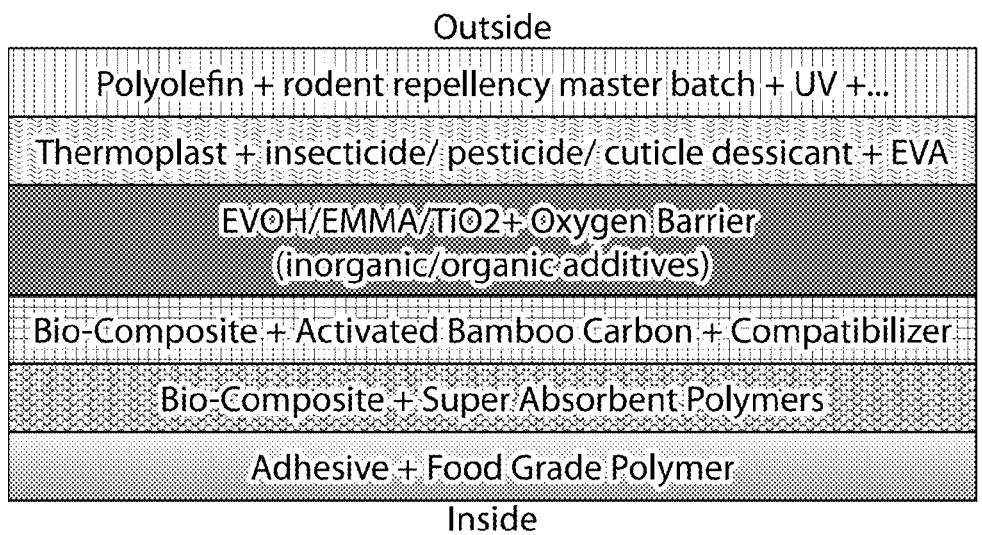
FIG. 1c is a schematic of a polymeric laminate in accordance with yet another alternative embodiment of the present invention.

FIG. 1c is a schematic of a polymeric laminate in accordance with yet another alternative embodiment of the present invention. This embodiment is similar to that of FIG. 1 except that arrangement of layers 4 and 5 has been reversed.

Figure 1D:
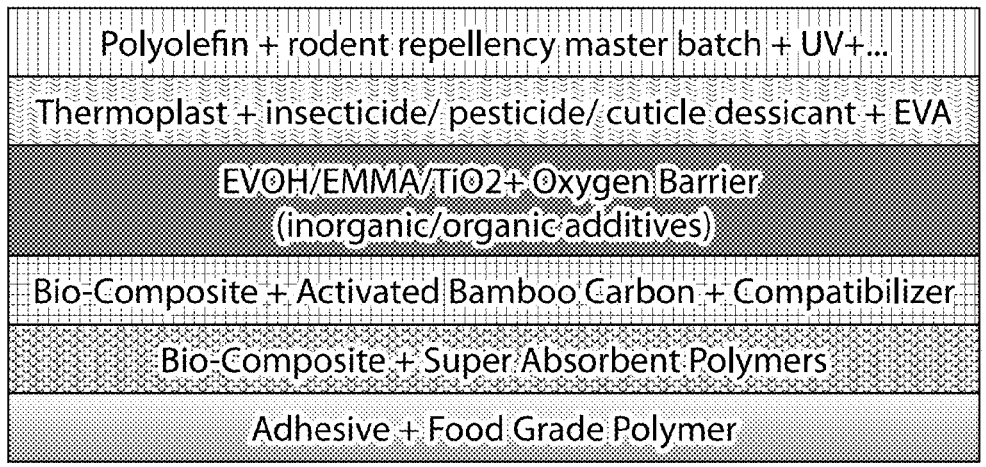
FIG. 1d is a schematic of a polymeric laminate in accordance with yet another alternative embodiment of the present invention.

FIG. 1d is a schematic of a polymeric laminate in accordance with yet another alternative embodiment of the present invention. This embodiment is similar to that of FIG. 1 except that layers 4 and 5 have been effectively combined by being coextruded as a single layer.

Figure 1E:
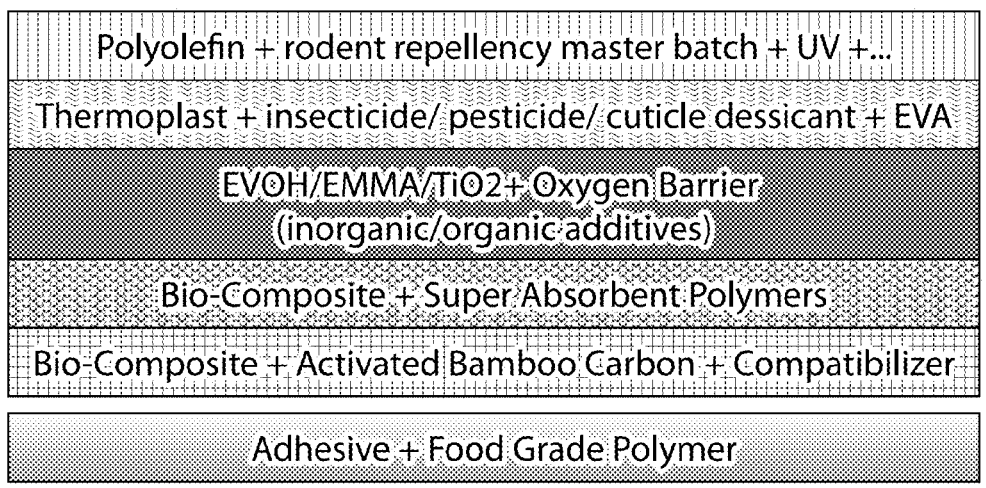
FIG. 1e is a schematic of a polymeric laminate in accordance with yet another alternative embodiment of the present invention.

FIG. 1e is a schematic of a polymeric laminate in accordance with yet another alternative embodiment of the present invention. This embodiment is similar to that of FIGS. 1-1d except that layer 6 is produced as a single layer and inserted as liner when the film is converted to a bag through the use of such techniques as horizontal or vertical form, fill and seal, or manually.

Figure 2:
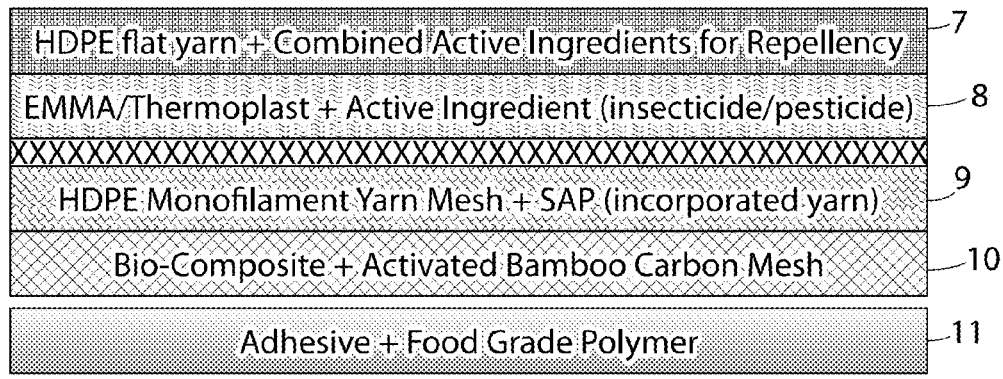
FIG. 2 is a schematic of a woven material laminate in accordance with one embodiment of the present invention.

FIG. 2 is a schematic of a woven material laminate in accordance with one embodiment of the present invention. This Figure shows outermost layer 1 which is a tape-woven layer 7 of an HDPE (or polypropylene) flat yarn containing the pesticide and rodent repellent ingredients which is thermally laminated with a EMMA thermoplastic layer 8 also containing a pesticide. It is preferred that the pesticide in the warp or weft of layer 7 be different from that of layer 8. Additionally, the warp (or weft) of layer 7 may contain the pesticide while the weft (or warp) of layer 7 contains the rodent repellent. The HDPE (or polypropylene) flat yarn may come from post-industrial or post-consumer recycled material.

FIG. 2 also shows the HDPE monofilament yarn mesh layer 9 which has the superabsorbent polymer chemically incorporated into the yarn. Layer 10 is a biocomposite mesh prepared from a monofilament yarn of HDPE with activated carbon contained in the polymer. Layer 11 is a sheet of food grade polymer with an adhesive to bind it to the mesh layer 10. The laminate of FIG. 2 is prepared by first assembling sub-laminates of layers 7 and 8 and 9-11, respectively, followed by thermal point bonding the two sub-laminates together, as indicated by the series of X's in FIG. 2.

Figure 2A:
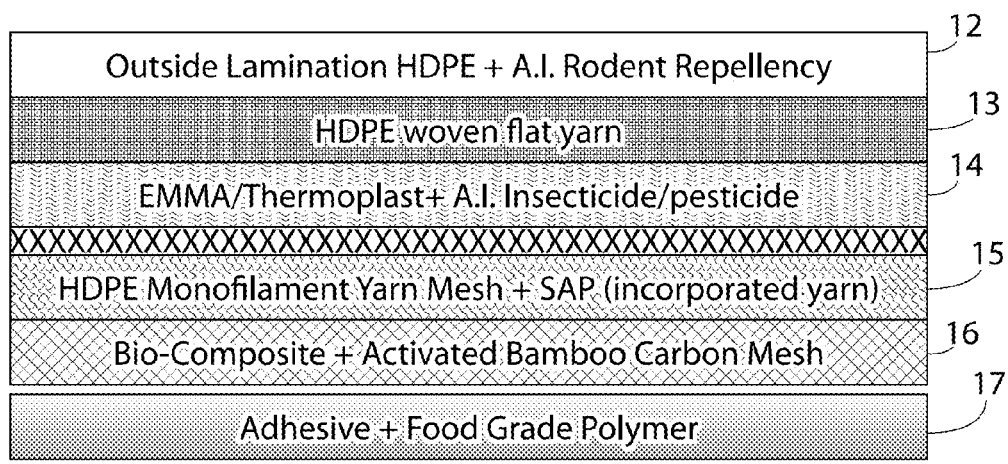
FIG. 2a is a schematic of a woven material laminate in accordance with an alternative embodiment of the present invention.

FIG. 2a is a schematic of a woven material laminate in accordance with an alternative embodiment of the present invention. This embodiment is similar to that of FIG. 2 except that layers 1 and 2 have been effectively combined by being coextruded as a single layer.

FIG. 2a is a schematic of a woven material laminate in accordance with an alternative embodiment of the present invention. This embodiment is similar to that of FIG. 2 except that the woven layer 13 contains no active ingredients while additional layer 12 laminated on the outside of the woven layer 13 contains a rodent repellent and layer 14 contains an insecticide. This embodiment also shows layers 15 and 16 that are similar to layers 9 and 10 of FIG. 2, and layer 17 that may be produced as a single layer and inserted as liner when the film is converted to a bag through the use of such techniques as horizontal or vertical form, fill and seal, or manually.

Figure 2B:
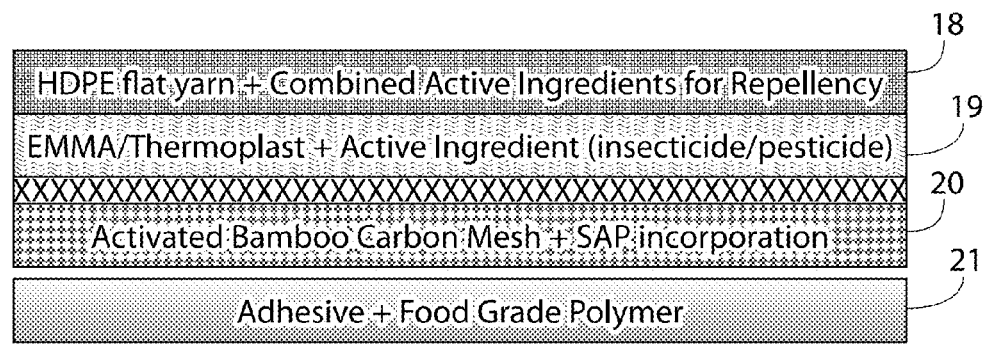
FIG. 2b is a schematic of a woven material laminate in accordance with yet another alternative embodiment of the present invention.

FIG. 2b is a schematic of a woven material laminate in accordance with yet another alternative embodiment of the present invention. This embodiment is similar to that of FIG. 2 with layers 18 and 19 similar to layers 7 and 8, and with the exception that layers 9 and 10 have been combined as a single layer 20, and layer 21 being produced as a single layer and inserted as liner when the film is converted to a bag through the use of such techniques as horizontal or vertical form, fill and seal, or manually.

Figure 2C:
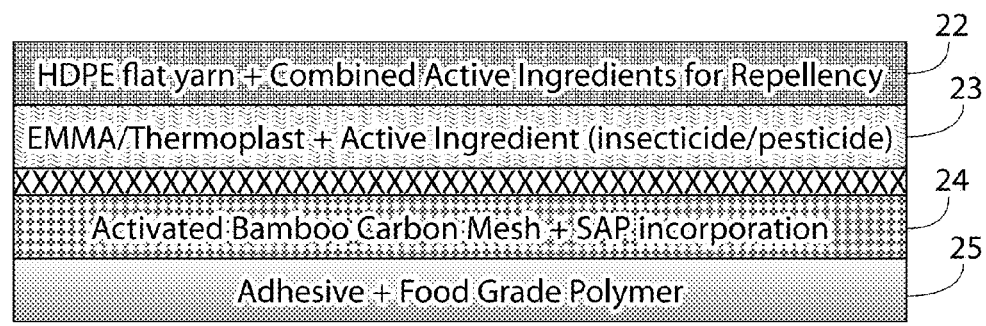
FIG. 2c is a schematic of a woven material laminate in accordance with yet another alternative embodiment of the present invention.

FIG. 2c is a schematic of a woven material laminate in accordance with yet another alternative embodiment of the present invention. This embodiment is similar to that of FIG. 2b with layers 24 and 25 being coextruded as a single sub-laminate prior to thermal point bonding.

Figure 3:
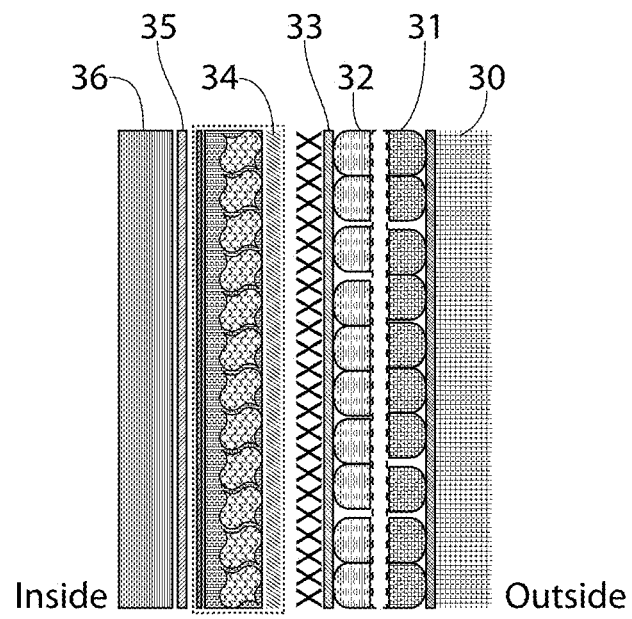
FIG. 3 is a schematic representation of the production of a polymeric laminate in accordance with one embodiment of the present invention.

FIG. 3 is a schematic representation of the production of a polymeric laminate formed in accordance with yet another alternative embodiment of the present invention. FIG. 3 shows outermost layer 30 which would be the same construction as layers 7 and 8 of FIG. 2. Layer 31 is a bubble plastic layer of LDPE, VLDPE, polypropylene or other suitable polymeric material, adhered to layer 30 by an adhesive such as EVOH, and wherein the bubbles are provided with an insecticide in powder form, such as diatomaceous earth (such as is sold under the trade name Protect-It from Headley Technologies) or other cuticle desiccant and may or may not include one or more of the synthetic pyrethroids or synthetic organophosphate insecticides or insect growth regulator.

Layer 32 is an opposing layer of bubble plastic (such as may be produced by thermoforming in combination with layer 31) wherein the bubbles are provided with a rodent repellent such as those described herein. Layer 33 is a separate layer of a thermoplastic material containing a filler/blocking agent (such as calcium carbonate) provided so as to prevent any liberated rodent repellent and/or insecticide/pesticide from migrating toward the food grade layer.

Layer 34 is a non-woven or other equivalent layer, such as a filter membrane, that encapsulates cellulosic or other naturally absorbent materials (such as coconut husks, apricot pits, and the like) and/or superabsorbent polymers, to provide a moisture barrier to retain and absorb moisture issuing from the contained foodstuff, such as that of transpiration of grain and the like.

Layer 35 is an adhesive layer, such as EVOH or other equivalent materials, such as those described herein. Layer 36 is a food grade polymer that is attached to layer 34 by adhesive layer 35. Layers 34/35/36 may then thermal point bonded to layers 30-33.

Figure 3A:
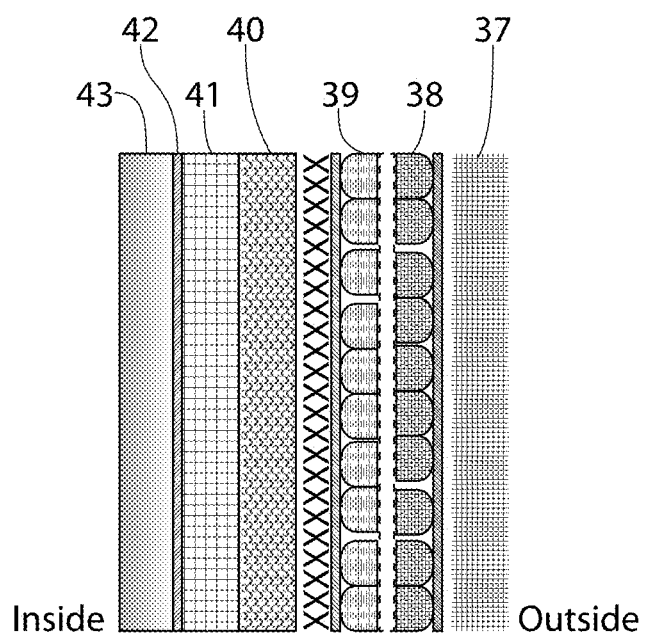
FIG. 3a is a schematic representation of the production of a polymeric laminate in accordance with one embodiment of the present invention.

FIG. 3a is a schematic representation of the production of a polymeric laminate formed in accordance with yet another alternative embodiment of the present invention. This embodiment is similar to that of FIG. 3 with layers 37, 38 and 39 being equivalent to layers 30, 31 and 32; and wherein layers 34 and 35 have been replaced with layers 40 and 41 which are the same as layers 4 and 5 of FIG. 1, and wherein layer 43 is the same as layer 6 of FIG. 1 with optional adhesive layer 42 where the food grade layer is separately produced.

Figure 4:
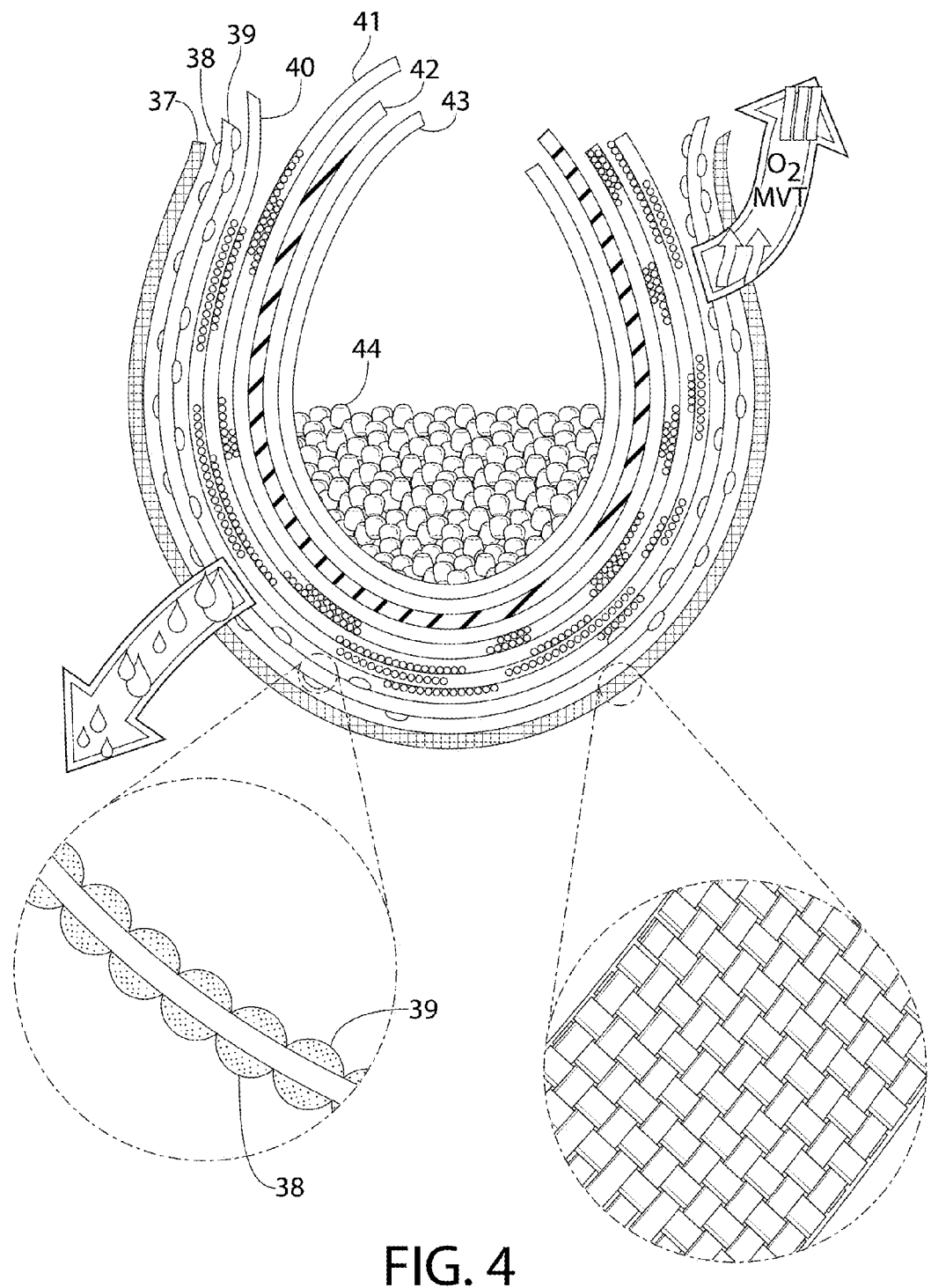
FIG. 4 is a schematic of a grain storage bag containing grain, in accordance with one embodiment of the present invention.

FIG. 4 is a schematic representation of the production of a polymeric laminate of the construction shown in FIG. 3a, and wherein like reference numerals indicate the respective layers, and formed into a bag and containing grain 44, in accordance with one embodiment of the present invention. This schematic shows the detailed construction of the cooperative layers 38 and 39 which provide an insecticide in powder form, and a rodent repellent, respectively.

It will be appreciated that the logical order of the steps are used for purposes of illustration only, and that the constituent layers, their measurements and active ingredient determinations may be varied where not otherwise inconsistent with the purpose and result obtained in the practice of the invention.

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

What is claimed is:

1. A polymeric laminate sheet material comprising:
   a. a first exterior layer comprising a thermoplastic polymeric material containing at least one rodent repellent material and an ultraviolet blocking material, and said thermoplastic polymeric material defining a plurality of spaces encapsulating one or more pesticide or insecticide;
   b. a second exterior layer comprising a food grade polymer and an adhesive; and, interposed between said first exterior layer and said second exterior layer, the following layers:
   c. an oxygen barrier intermediate layer comprising a thermoplastic polymeric material containing at least one additive that functions as a desiccant, a free radical scavenger or an oxygen barrier; and
   d. a bio-composite absorbent/compatibilizer layer comprising a thermoplastic polymeric material containing at least one super-absorbent polymer and activated carbon.

2. A polymeric laminate sheet material according to claim 1 wherein said bio-composite absorbent/compatibilizer layer comprises a first layer comprising at least one super-absorbent polymer; and a second layer comprising activated bamboo carbon.

3. A polymeric laminate sheet material according to claim 1 wherein said first exterior layer comprises a rodent repellent selected from the group consisting of synthetic pyrethroids.

4. A polymeric laminate sheet material comprising:
   a. a first exterior layer comprising a polyolefin, a rodent repellent and an ultraviolet blocking material;
   b. a second exterior layer comprising a food grade polymer and an adhesive; and, interposed between said first exterior layer and said second exterior layer, the following layers:
   c. an insecticide/pesticide intermediate layer comprising a thermoplastic polymeric material defining a plurality of spaces encapsulating one or more pesticide or insecticide;
   d. an oxygen barrier intermediate layer comprising a thermoplastic material selected from the group consisting of ethylene vinyl alcohol and ethylene methyl acrylic copolymer, and containing at least one oxygen barrier additive;
   e. a bio-composite absorbent layer comprising super-absorbent polymers; and
   f. a bio-composite compatibilizer layer comprising activated bamboo carbon and a compatibilizer.

5. A polymeric laminate sheet material according to claim 4 wherein said first exterior layer comprises a polyolefin selected from the group consisting of polypropylene, HDPE, LDPE, LLDPE, VLDPE and copolymers and homopolymers thereof.

6. A polymeric laminate sheet material according to claim 4 wherein said first exterior layer comprises a rodent repellent selected from the group consisting of synthetic pyrethroids.

7. A polymeric laminate sheet material according to claim 4 wherein said bio-composite compatibilizer layer comprises a compatibilizer selected from the group consisting of chitin and citric acid.

8. A polymeric laminate sheet material comprising:
   a. a first exterior layer comprising a polyolefin and an ultraviolet blocking material, said polyolefin defining a plurality of spaces encapsulating (a) at least one insecticide or pesticide material and (b) a cuticle desiccant;
   b. a second exterior layer comprising a food grade polymer and an adhesive; and, interposed between said first exterior layer and said second exterior layer, the following layers:
   c. a rodent repellent intermediate layer comprising ethyl vinyl acetate and a thermoplastic polymeric material, said thermoplastic polymeric material defining a plurality of spaces encapsulating a rodent repellent material;
   d. an oxygen barrier intermediate layer comprising a thermoplastic material selected from the group consisting of ethylene vinyl alcohol and ethylene methyl acrylic copolymer, and containing at least one oxygen barrier additive;
   e. a bio-composite absorbent layer comprising super-absorbent polymers; and
   f. a bio-composite compatibilizer layer comprising activated bamboo carbon and a compatibilizer.

9. A polymeric laminate sheet material according to claim 1 wherein said first exterior layer comprises a rodent repellent comprising permethrin.

10. A polymeric laminate sheet material according to claim 4 wherein said first exterior layer comprises a rodent repellent comprising permethrin.

11. A polymeric laminate sheet material comprising:
 a. a first exterior layer comprising a first layer comprising a polyolefin, said polyolefin comprising a rodent repellent and an ultraviolet blocking material; and a second layer comprising a thermoplastic polymeric material said thermoplastic polymeric material defining a plurality of spaces encapsulating at least one pesticide or insecticide;
 b. a second exterior layer comprising a food grade polymer and an adhesive; and, interposed between said first exterior layer and said second exterior layers, the following layers:
 c. an oxygen barrier intermediate layer comprising a thermoplastic polymeric material containing at least one additive that functions as a desiccant, a free radical scavenger or an oxygen barrier; and
 d. a bio-composite absorbent/compatibilizer layer comprising a thermoplastic polymeric material containing at least one super-absorbent polymer and activated carbon.

12. A polymeric laminate sheet material according to claim 11 wherein said first exterior layer comprises a polyolefin selected from the group consisting of polypropylene, HDPE, LDPE, LLDPE, VLDPE and copolymers and homopolymers thereof.

13. A polymeric laminate sheet material according to claim 11 wherein said bio-composite absorbent/compatibilizer layer comprises a first layer comprising at least one super-absorbent polymer; and a second layer comprising activated bamboo carbon.

14. A polymeric laminate sheet material according to claim 11 wherein said first exterior layer comprises a rodent repellent selected from the group consisting of synthetic pyrethroids.

15. An agricultural product storage container having an inner surface and formed from a polymeric laminate sheet material according to claim 1, and wherein said inner surface comprises said second exterior layer.

16. An agricultural product storage container having an inner surface and formed from a polymeric laminate sheet material according to claim 4, and wherein said inner surface comprises said second exterior layer.

17. An agricultural product storage container having an inner surface and formed from a polymeric laminate sheet material according to claim 8, and wherein said inner surface comprises said second exterior layer.

18. An agricultural product storage container having an inner surface and formed from a polymeric laminate sheet material according to claim 11, and wherein said inner surface comprises said second exterior layer.

* * * * *